Figure 1:
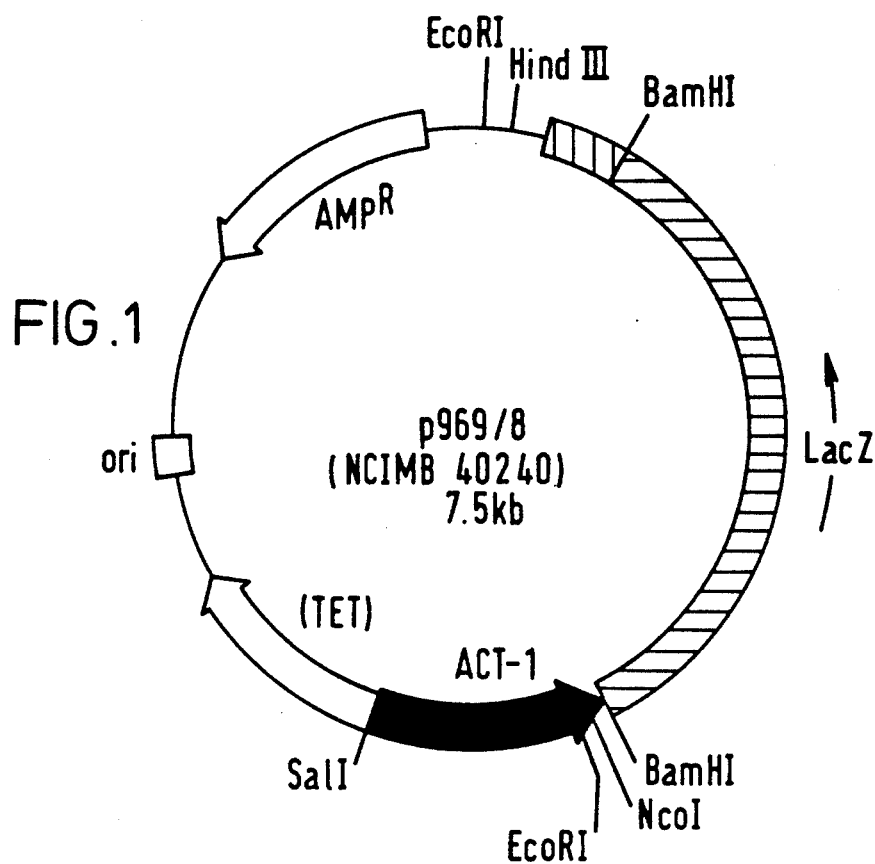

United States Patent [19]

Dykes et al.

[11] Patent Number: 5,238,822

[45] Date of Patent: Aug. 24, 1993

[54] GENE EXPRESSION IN YEAST CELLS

[75] Inventors: Colin W. Dykes, Greenford, United Kingdom; Joachim F. Ernst, Hilden, Fed. Rep. of Germany; Adrian N. Hobden, Harefield, United Kingdom

[73] Assignee: Glaxo Group Limited, London, England

[21] Appl. No.: 650,871

[22] Filed: Feb. 5, 1991

[30] Foreign Application Priority Data

Feb. 9, 1990 [GB] United Kingdom ............... 9003010

[51] Int. Cl.$^5$ ................... C12N 1/19; C12N 15/49; C12N 15/81

[52] U.S. Cl. ................ 435/69.1; 435/172.3; 435/320.1; 435/942; 435/254.21; 536/23.72; 536/24.1; 935/37; 935/69

[58] Field of Search ............... 435/69.1, 172.3, 256, 435/320.1; 536/27, 23.72, 24.1

[56] References Cited

U.S. PATENT DOCUMENTS

| | | | |
|---|---|---|---|
| 4,405,712 | 9/1983 | Woude et al. | 435/5 |
| 4,981,790 | 1/1991 | Haseltine et al. | 435/69.1 |

FOREIGN PATENT DOCUMENTS

| | | |
|---|---|---|
| 0291893A1 | 11/1988 | European Pat. Off. |
| 0331356A2 | 9/1989 | European Pat. Off. |
| 0352060A2 | 1/1990 | European Pat. Off. |
| WO85/05636 | 12/1985 | PCT Int'l Appl. |
| WO87/02989 | 5/1987 | PCT Int'l Appl. |
| WO88/07083 | 9/1988 | PCT Int'l Appl. |
| WO90/08780 | 8/1990 | PCT Int'l Appl. |

OTHER PUBLICATIONS

R. Toyama et al (1992) Nucleic Acids Research 20(10):2591-2596.
Rosen et al, Cell, 41, pp. 813-823, Jul. 1985.
Fisher et al, Nature, 320, pp. 367-371, Mar. 27, 1986.
Cullen, Cell, 46, pp. 973-982, Sep. 26, 1986.
Wright et al, Science, 234, pp. 988-992, Sep. 17, 1986.
Barr et al, Biotechnology, No. 5, pp. 486-489, May 1987.
Green et al, Cell, 58, pp. 215-223, Jul. 14, 1989.
Thiele et al, Molecular and Cellular Biology, 4, No. 1, pp. 92-100, Jan. 1984.
Berkhout et al, Cell, 59, No. 2, pp. 273-282, Oct. 20, 1989.
Laspia et al, Cell, 59, Nos. 2, pp. 283-292, Oct. 20, 1989.
Kuppuswamy et al, Nucleic Acids Research, 17, No. 9, pp. 3551-3561, May 11, 1989.
Mertins et al, Nucleic Acids Research, 15, No. 18, pp. 7369-7378, Aug. 28, 1987.
Wong-Staal, NTIS Report No. Pat-Appl-7-306 612, 1989.

Primary Examiner—Richard A. Schwartz
Assistant Examiner—Johnny F. Railey, II
Attorney, Agent, or Firm—Bacon & Thomas

[57] ABSTRACT

A transformed yeast cell containing the following DNA sequences,
- an HIV tat gene coding for a TAT protein,
- a first promoter exercising transcriptional control over the tat gene,
- an HIV regulatory control sequence which is responsive to the TAT protein,
- a pre-selected gene coding for a desired polypeptide or protein, the pre-selected gene being under the control of the HIV regulatory control sequence, and
- a second promoter exercising transcriptional control over the HIV regulatory control sequence and the pre-selected gene.

Preferably the first and second promoters are yeast promoters, the transformed yeast cell is a S.cerevisiae cell and the HIV regulatory control sequence is a TAT responsive TAR sequence.

The transformed yeast cells may be used to screen for agents that inhibit the function of TAT protein.

14 Claims, 5 Drawing Sheets

GENE EXPRESSION IN YEAST CELLS

The human immunodeficiency virus-1 (HIV-1) is the primary etiologic agent of the acquired immune deficiency syndrome (AIDS). In addition to the gag, pol and env genes that encode the major virus structural proteins, the genome of HIV contains several other open reading frames designated, for example tat, rev and nef which encode additional viral proteins. These proteins are known to serve important regulatory functions during the HIV infectious cycle.

One important regulatory protein, TAT, the product of the tat gene, mediates the activation of the expression of gene sequences linked to the HIV-LTR (long terminal repeat) promoter region. This positive control of gene expression by the TAT protein is an example of a phenomenon termed trans-activation. Trans-activation refers to the positive regulation of the expression of specific target gene by a specific regulatory protein.

The sequence information within the HIV-LTR that is responsive to trans-activation by TAT resides between nucleotides −17 and +80 (numbering is relative to the transcription start site). This sequence, within HIV-LTR, is known as the TAR (trans-acting responsive or target) sequence.

In the present specification the phrase "a TAT responsive TAR sequence" refers to any DNA sequence (naturally derived or synthethically derived) based on the sequence between −17 and +80 of HIV-LTR that responds to trans-activation by the TAT protein.

Previously, gene expression under the control of a TAT activated HIV regulatory control sequence has been effected in mammalian cells. Indeed, it was widely suggested that, for proper gene expression/TAT activation, mammalian host cell factors were required (see, for example, C. M. Wright et al, Science, 1986, 234 988 and B Berkhout et al Cell, 1989, 59, 273).

Surprisingly, it has now been found that TAT-activated gene expression may also be conducted in yeast cells, in particular Saccharomyces cerevisiae.

Therefore, according to a first aspect of the present invention, there is provided a transformed yeast cell containing the following DNA sequences,
  an HIV tat gene coding for a TAT protein,
  a first promoter exercising transcriptional control over the tat gene,
  an HIV regulatory control sequence which is responsive to the TAT protein,
  a pre-selected gene coding for a desired polypeptide or protein, the pre-selected gene being under the control of the HIV regulatory control sequence,
  and a second promoter exercising transcriptional control over the HIV regulatory control sequence and the pre-selected gene.

The yeast cells chosen to be transformed may be, for example, from the genus Candida, Schizosacharomyces or, which is preferred, Saccharomyces. In a particularly preferred embodiment of the present invention, the species Saccharomyces cerevisiae is employed.

The HIV tat gene may be derived from natural sources or produced synthetically. It, the HIV tat gene, must code for either a TAT protein or a fragment of a TAT protein. In either case, the TAT protein/fragment must trans-activate the HIV regulatory control sequence. In a preferred embodiment of the present invention, a synthetic 256 base-pair tat gene, closely corresponding to the two spliced tat exons in the λBH10 isolate (L. Ratner et al, Nature, 1985, 313. 277) is employed. In this preferred, synthetic gene, the following alterations are made to the naturally occurring λ BH10 sequences, Arg 7 Codon (AGA) changed to CGT, Tyr47 Codon (TAT) changed to TAC, Arg 55 Codon (CGA) changed to CGT. Finally, a NcoI site is placed at a position corresponding to the translational start codon (CCATGG).

The first and second promoter may be the same or different. They must both exercise transcriptional control over their respective genes, (the first promoter over the tat gene, the second promoter over the HIV regulatory control sequence and the pre-selected gene), when expression is taking place in yeast cells. In certain circumstances, a non yeast promoter, carrying transcriptional control elements which function in yeast may be used as the first and/or second promoter. More commonly, however, the first and/or second promoter is (are) a yeast promoter. Suitable yeast promoters include ura 3, arg 3, pgk, trp 1, adh 1, gal 10, cvc 1, α-factor and act-1. Of these yeast promoters, qal 10, cyc 1 and α-factor are preferred for use as the first promoter, whilst act-1 is preferred for use as the second promoter.

The HIV regulatory control sequence must be responsive to the TAT protein and must control the expression of the pre-selected gene. The regulatory control sequence may be obtained from natural sources or may be produced synthetically. Generally, it will comprise a TAT responsive HIV-LTR sequence. In a preferred embodiment of the present invention the HIV regulatory control sequence is the TAR sequence found in the HIV-LTR.

In a particularly preferred embodiment of the present invention, the HIV regulatory control sequence is a synthetic TAR sequence corresponding to the 97 base-pair Pvu II -Hind III TAR fragment of λBH10.

The pre-selected gene may be any gene, the expression of which it is desired to enhance. In most cases, the expressed polypeptide or protein will be heterologous to the yeast cell. Suitable polypeptides/proteins include enzymes, lymphokines, hormones, antigenic proteins, peptides and glycopeptides.

In a particularly preferred embodiment of the present invention, the desired protein is an indicator protein, the concentration of which may be readily measured, using known assay procedures. Suitable examples of such proteins are bacterial chloramphenicol acetyl transferase, E. coli beta-galactosidase and human interleukin 2 (IL2).

In an alternative preferred embodiment, the polypeptide protein expressed is toxic to the yeast cell. In this case full TAT activated expression of the pre-selected genes would inhibit cell growth. If, however, TAT function were itself inhibited, then cell growth would be greater.

In order to facilitate the introduction of the required DNA sequences into a yeast cell, there is provided, in a second aspect of the present invention, a gene expression system comprising
  an HIV tat gene coding for a TAT protein,
  a first yeast promoter exercising transcriptional control over the tat gene,
  an HIV regulatory control sequence which is responsive to the TAT protein,
  a pre-selected gene coding for a desired polypeptide or protein, the pre-selected gene being under the control of the HIV regulatory control sequence, and a second yeast promoter exercising transcriptional control over the HIV regulatory control sequence and the pre-selected gene.

Generally, the gene expression system will consist of one or two, especially one, transfer vector(s). Preferably the transfer vector(s) is/are yeast transfer vector(s). Suitable yeast transfer vectors fall within the classes, yeast integrating plasmid (YIp, e.g. YIp lac 204, YIp lac 211, YIp lac 128 (Geitz and Sugino, Gene, 1988, 74,527–534 ), yeast episomal plasmid (YEp, e.g. YEp lac 112, YEp lac 195, YEp lac 181 (Geitz and Sugino), pEX-2dECO(vide infra), yeast replicating plasmid (YRp) or yeast centromeric plasmids (YCp, e.g, YCp lac 22, YCp lac 33, YCp lac III (Geitz and Sugino), pJDCEN6 (vide infra).

If the required DNA sequences are placed in separate vectors, then the HIV tat gene and the first promoter will reside in one vector, whilst the HIV regulatory control sequence, the pre-selected gene and the second promoter will reside in a second vector. In this case, the first and second promoters may be the same or different. If on the other hand, the required DNA sequences are placed on a single vector, then the first and second yeast promotors will be different.

In addition to the required DNA sequences, the gene expression system may also contain markers, such as Leu2+, His+, Ura3+ or Trpl+, that can be selected readily in yeast. In this case, the yeast strain chosen will generally be unable, in the absence of plasmid to produce the marker compound, e.g leucine, histidine, uracil, tryptophan. In addition, the system may also carry antibiotic resistance markers. The system may contain the yeast, especially the *S. cerevisiae*, 2μ origin of replication. Finally, the system may also contain *E. coli* origin of replication to allow genetic manipulation in *E. coli*.

In a further aspect of the present invention, there is provided a method of producing a desired polypeptide or protein comprising cultivating a transformed yeast cell according to the present invention.

In a still further aspect of the present invention, there is provided & method of obtaining TAT protein mediated expression of a pre-selected gene under the control of an HIV regulatory control sequence which comprises cultivating a transformed yeast cell according to the present invention.

The tat gene product is known to be essential for HIV replication. Since TAT is an essential and virus - specific component of the HIV life cycle, specific inhibitors of TAT function are likely to be important anti-HIV viral therapeutic agents. The present invention therefore provides, in a still further aspect of the present invention, a method of screening potential agents (especially potential anti-viral agents) that may specifically interfere with HIV TAT function. The ability to identify agents that selectively attack a virus without harming the mammalian host, offers the potential for effective, yet non-toxic anti-viral drugs.

According to another aspect of the present invention, therefore, there is provided a method of screening agents which may inhibit the function of a TAT protein, which comprises cultivating a transformed yeast cell according to the present invention in the presence of an agent and measuring the level of expression of the pre-selected gene.

Figure 2:
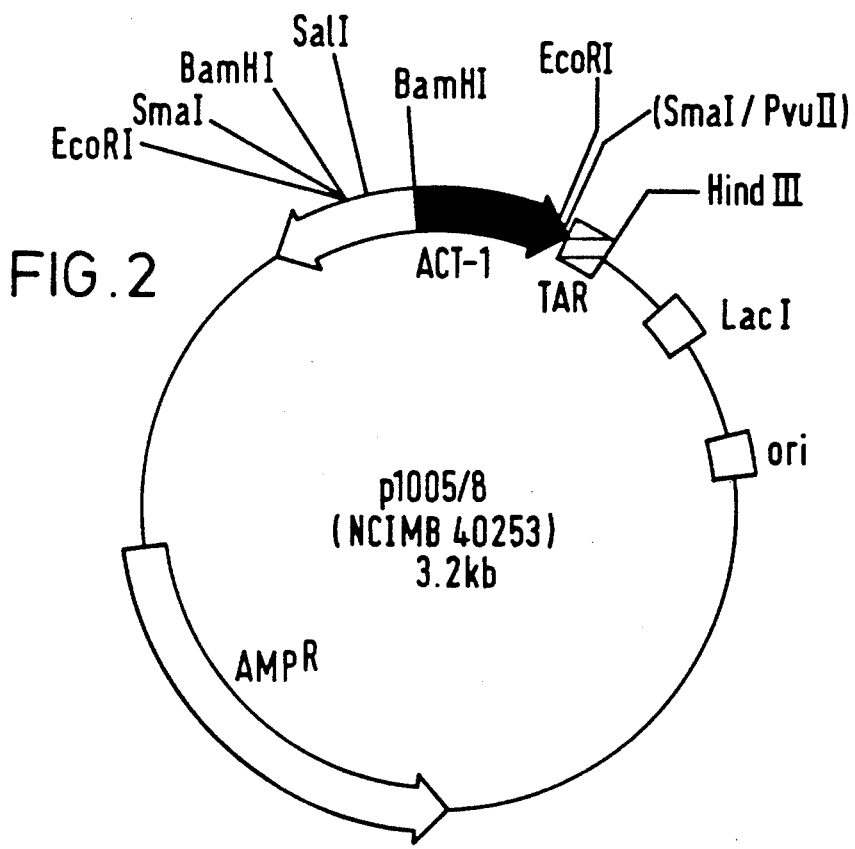
Figure 3:
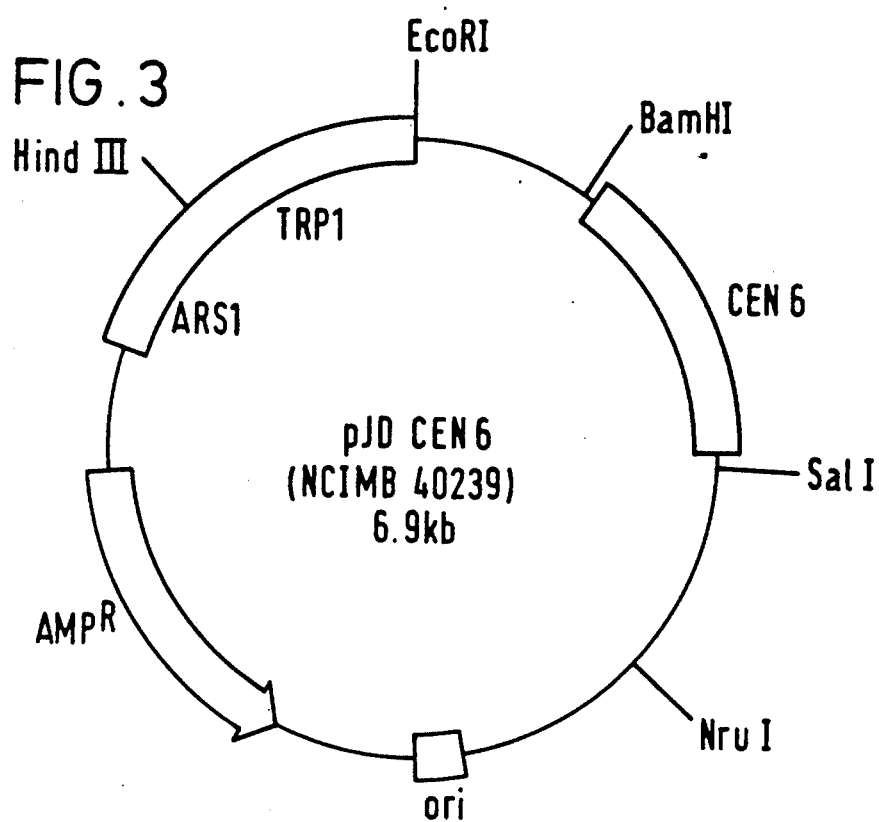
Figure 4:
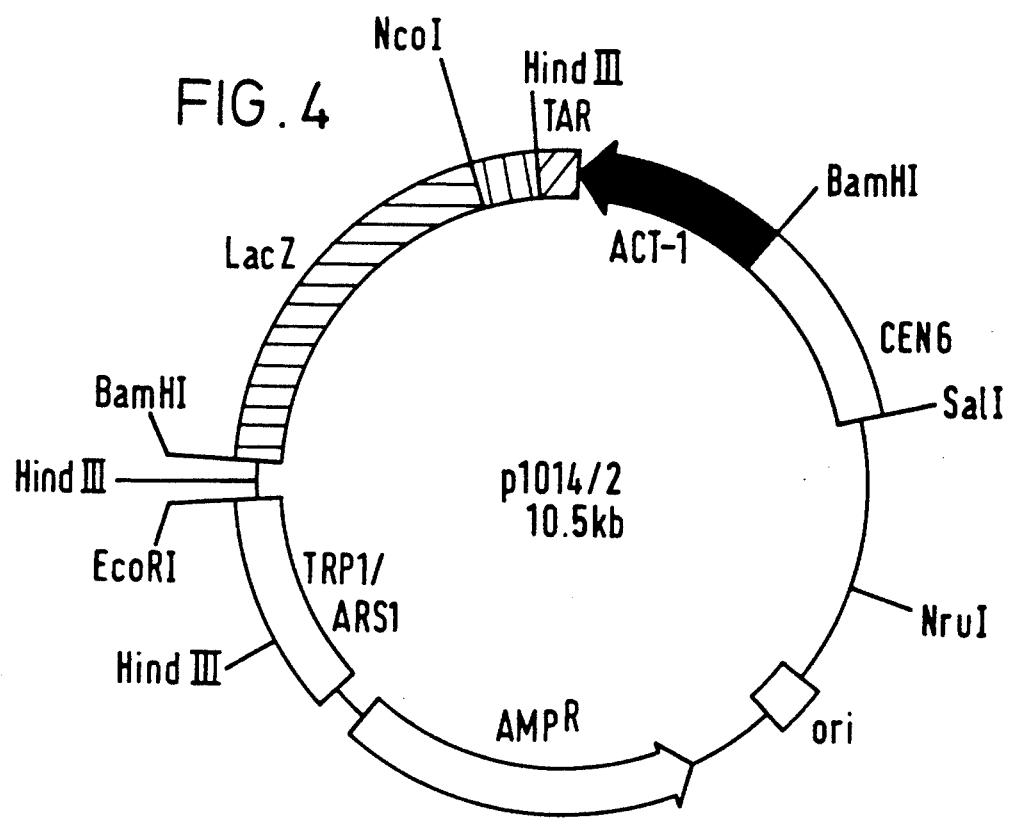
Figure 5:
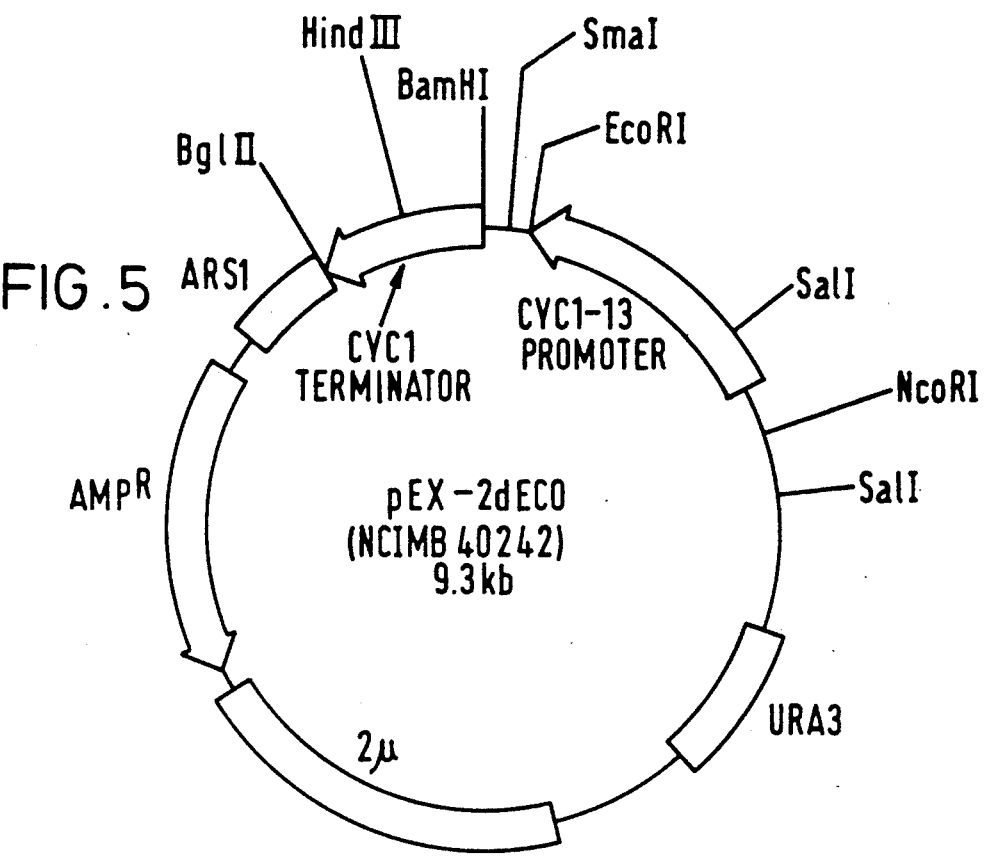
Figure 6:
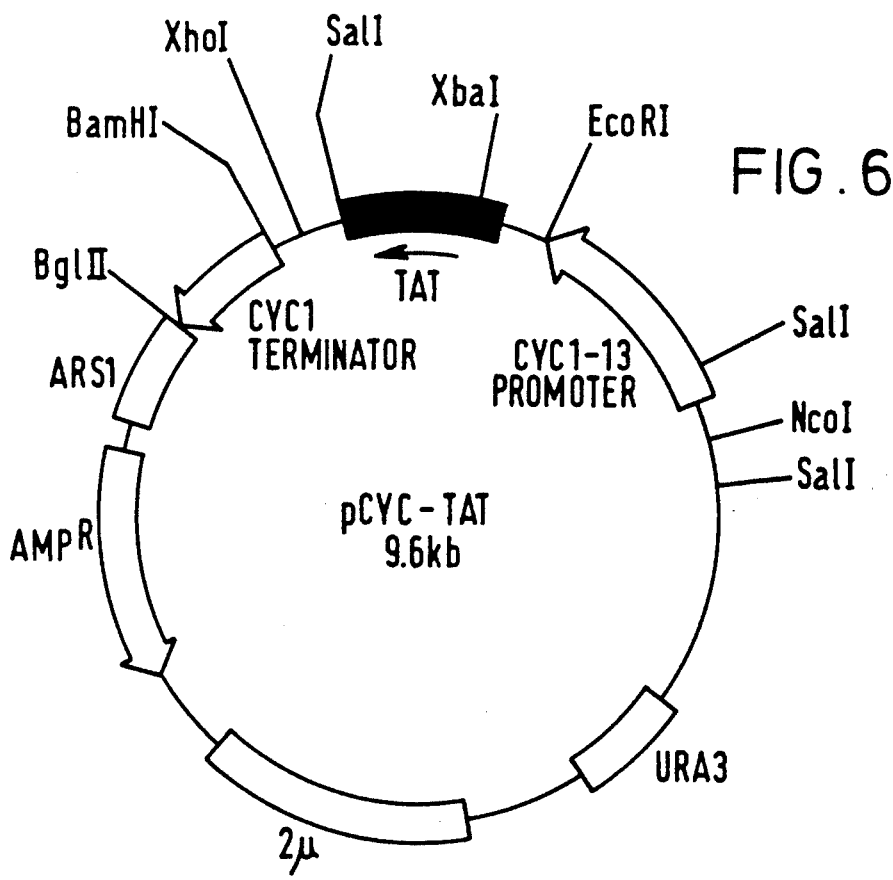
Figure 7:
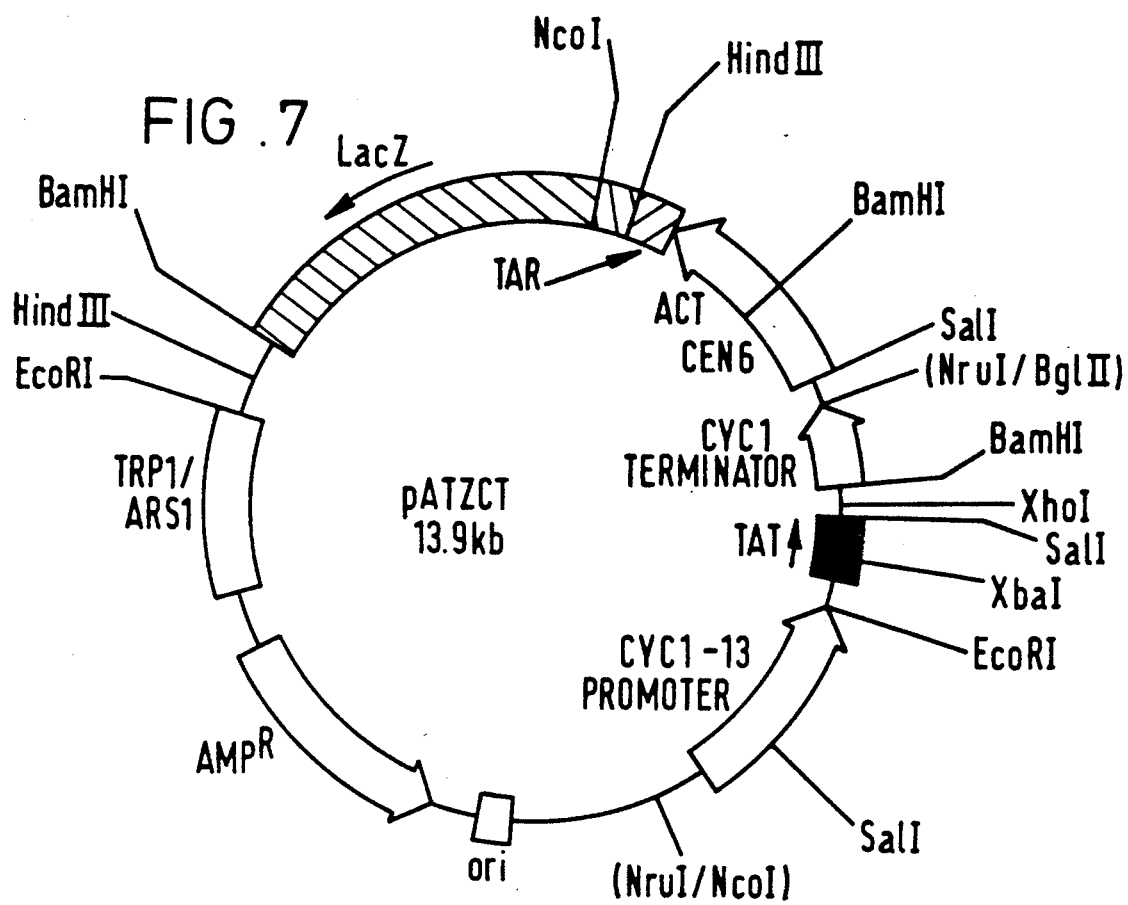
Figure 8:
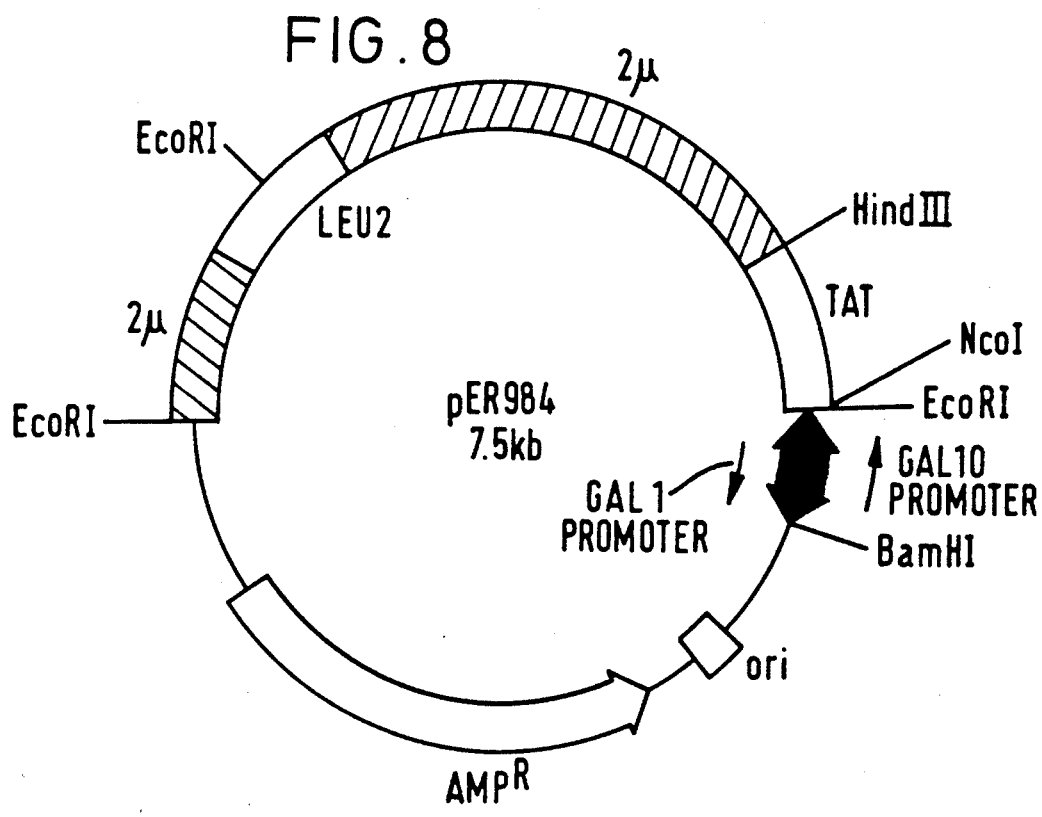
Figure 9:
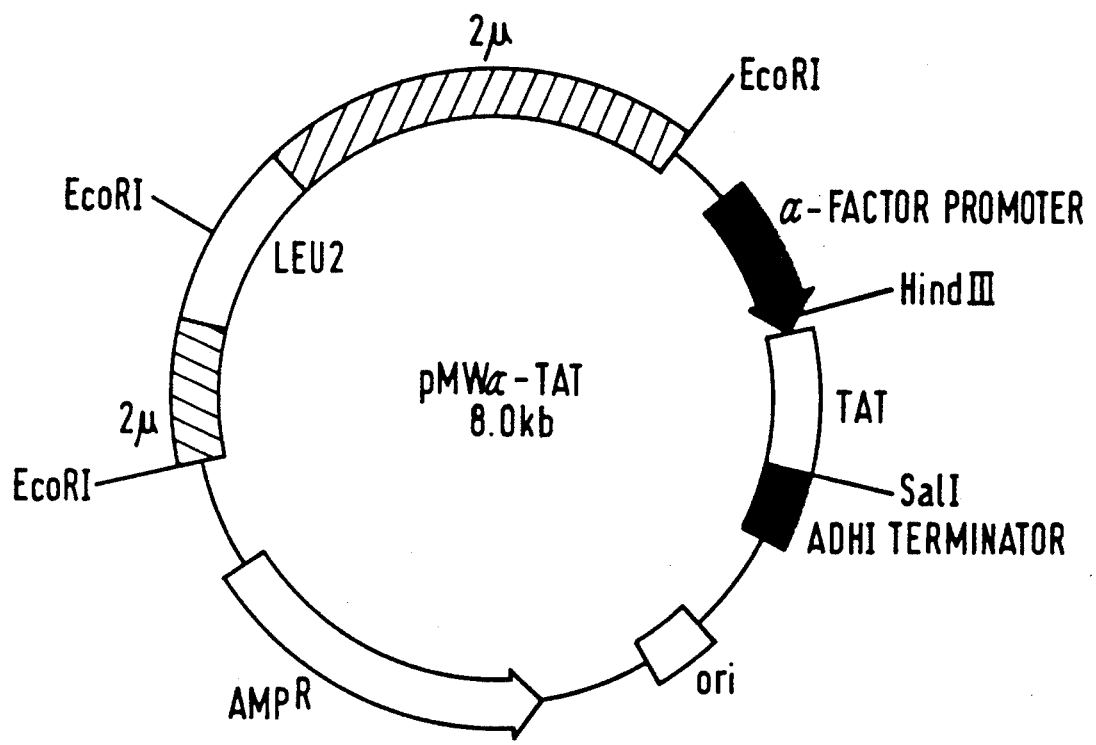

The present yeast cells, gene expression system and methods will now be described by way of example only and with particular reference to the Figures in which:

FIG. 1 represents the plasmid p969/8 (NCIMB 40240),
FIG. 2 represents the plasmid plO05/8,(NCIMB 40253),
FIG. 3 represents the plasmid pJD CEN 6 (NCIMB 40239),
FIG. 4 represents the plasmid plO14/2,
FIG. 5 represents the plasmid pEX-2dECO (NCIMB 40242),
FIG. 6 represents the plasmid pCYC-TAT,
FIG. 7 represents the plasmid pAT ZCT,
FIG. 8 represents the plasmid pER 984,
FIG. 9 represents the plasmid pMWα-TAT.

In the Figures, (TET) means that only part of the $TET^R$ gene is present and that it no longer affords resistance to tetracycline.

MATERIALS

X-Gal (5-bromo-4-chloro-3-indolyl-β-galactopyranoside), CPRG (chlorophenol red-β-D-galactopyranoside) and the enzymes Bam HI, Bgl II, Eco RI, Eco Rv, Hind III, NcoI, NruI, PstI, PvuII, sacI (SstI), SalI, smaI, DNA polymerase Klenow fragment, polynucleotide kinase and DNA ligase were obtained from Boehringer Corporation (London). Plasmids pUC-9, pBR322 and M13 vectors were obtained from Pharmacia. dATP, dCTP, dGTP,dTTP, ddATP, ddCTP, ddGTP, and ddTTP were also obtained from Pharmacia. *E.coli* JM103 and DHI were obtained from GIBCO-BRL [γ-32P]- ATP and [α-thio$^{35}$S]- dATP were obtained from Amersham International. Phosphate Buffered Saline (Dulbecco "A") tablets were obtained from Oxoid Ltd and were used in accordance with the manufacturers' instructions. Glass beads (0.4 mm, 40 mesh) were obtained from BDH Chemicals Ltd.

METHODS

DNA Manipulations, including ligations and transformation of *E.coli* strains, were performed essentially as described by Maniatis etal) Molecular Cloning, Cold Spring Harbor New York, 1982). Restriction endonuclease digestions were performed using conditions recommended by the suppliers. The nucleotide sequences of synthetic DNA fragments were determined by the M13 dideoxy sequencing method (M. D Biggin et al, Proc Natl. Acad Sci, 1983, 80, 3963).

1) Preparation of synthetic DNA sequences

The tat gene and the TAR segment were assembled using overlapping synthetic fragments. These (overlapping) fragments were prepared by means of a Biosearch model SAMI (trade mark) DNA synthesiser using β-cyanoethyl phosphoramidites (N. D Sinha et al, Nucleic Acids Res., 1984 12, 4539).

Methods for the purification of synthetic oligonucleotides, their ligation into M13 vectors, and the transformation of *E.coli* JM103 using the subsequently formed plasmids are described in UK Patent Application No. 2180539A. The contents of which publication are hereby incorporated by reference.

a) Tat Gene sequence

The sequence of the coding strand of the synthetic tat gene is given in Table 1. It differs from authentic tat of the HIV-1 λBH10 variant at codons for Arg 7 (AGA to CGT, to create an XbaI site), Tyr 47 (TAT to TAC) and Arg 55 (CGA to CGT).

The individual oligonucleotides used to prepare the synthetic tat gene are shown in Table 2. It can be seen from the sequences that, in order to facilitate cloning, the synthetic tat gene (Table 1) has, in addition,
i) a Nco I site placed at a position corresponding to the translational start codon (CCATGG),
ii) an sstI (SacI) overhang at the 5,-end, and
iii) a Pst I overhang at the 3,-end.

The presence of the SstI and PstI overhangs allows the convenient cloning of the tat gene into the vector M13 mpII (Pharmacia) to produce plasmid mpII - TAT.

The gene was cloned in two portions. Oligonucleotides TAT/1A, TAT/2A, TAT/3A, TAT/1B, TAT/2B and TAT/3B were ligated together to produce portion which was then inserted into M13 mpII using the sstI (Sac I) and Sal I sites. E.coli JM103 was used as the host for cloning using M13 vectors. Oligonucleotides TAT/4A, TAT/5A, TAT/4B and TAT/5B were then ligated together (portion 2) and inserted between the SalI and PstI sites of the M13-TAT(portion 1) clone to produce plasmid mpII - TAT. Insertion of the portion 2 fragment destroyed the SalI site at the end of portion 1 leaving the Sal I site at the end of portion 2 unique within mpII-TAT.

b) HIV TAR Sequence

The TAT responsive HIV TAR sequence was also prepared as a synthetic fragment. Oligonucleotides TAR/1A, TAR/2A, TAR/1B and TAR/2B (Table 3) were ligated together and inserted between the Eco RI and Hind III sites of M13 mpII to produce mpII - TAR. The TAR sequence could then be excised as a Pvu II - Hind III fragment.

CONSTRUCTION OF PLASMIDS

Plasmids constructed (and certain of those used in construction) are illustrated in FIGS. 1 to 9. Restriction sites destroyed by ligation of "filled-in" ends are shown in parentheses. E.coli DHI was used as host for transformation of ligation mixtures. With the exception of M13 clones, all other plasmids carried the beta-lactamase gene and transformed DHI cells were selected by their ability to grow on L B Plates containing ampicillin.

a) Plasmis p969/8 (FIG. 1, MCIMB 40240)

The act-1 promoter (from plasmid p YAT), as a Bam HI fragment, was ligated into the Bam HI site of pUC-9 (Pharmacia). The ligation mix was transformed into E.Coli DHI and transformants were selected on LB - AMP plates, as described in Maniatis et al. Small scale plasmid preparations were prepared from individual clones and these were subjected to restriction analysis to identify a clone which carried the 5'- end of the act -1 promoter adjacent to the SalI site of pUC-9. One such plasmid designated p921/1, was modified by deletion of the 5'-BamHI site. To achieve this, p921/1 was first subjected to partial digestion with Bam HI, followed by treatment with DNA polymerase Klenow fragment and was then religated and transformed into DHI. Loss of the 5'-Bam HI site was confirmed by restriction mapping. The resulting plasmid was designated p941/3.

The act-1 promoter was taken from p941/3 as a SalI-Bam HI fragment and joined to the Bam HI-BalI Lac Z fragment of pMC1790. This combined sequence was then inserted between the salI and EcoRV sites of pBR322. In the resulting plasmid, p969/8, a new Bam HI site is created by the ligation of the BalI end of the Lac Z gene to the EcoRV site of pBR322. Transformed E.coli DHI cells containing plasmid p969/8 were deposited under the terms of the Budapest Treaty at the National Collection of Industrial and Marine Bacteria (Torry Research Station, P.O. Box 31, 135 Abbey Road, Aberdeen AB9 8DG) on Dec. 20, 1989 under accession number NCIMB 40240.

b) Plasmid pl005/8 (FIG. 2)

Plasmid pl005/8 was prepared by inserting a SalI-smaI fragment containing the act-1 promoter and the synthetic 97 base pair Pvu II - Hind III TAR fragment from mpII-TAR between the SalI and Hind III sites of pUC-9. The ligation of the SmaI end of the act-1 fragment to the Pvu II end of the TAR fragment destroyed both sites.

Transformed E.Coli DHI cells containing plasmid plO05/8 were deposited under the terms of the Budapest Treaty at the National Collection of Industrial and Marine Bacteria on Jan. 31, 1990 under accession number NCIMB 40253.

c) Plasmid p1014/2 (FIG. 4)

The "ACT-TAR" region was released from plasmid p1005/8 by digestion with Bam HI and Hind III. The 600bp "ACT-TAR" fragment, the large EcoRI - Bam HI fragment from pJDCEN6 and the 3kb Lac Z fragment from p969/8 were then all purified by band excision from preparative agarose gels.

The "ACT-TAR" fragment was then ligated to the NcoI-EcoRI LacZ fragment from plasmid p 969/8 (NCIMB 40240) via a synthetic Hind III-NcoI linker (shown below)

Hind III  5' - AGCTTCTAGAC

AGATCTGGTAC - 5' NcoI

The entire fragment was then inserted between the Bam HI and EcoRI sites of pJD - CEN6 (FIG. 3, NCIMB 40239) to produce plasmid p1014/2.

Transformed E.coli DHI cells containing plasmid pJD-CEN6 were deposited under the terms of the Budapest Treaty at the National Collection of Industrial and Marine Bacteria on Dec. 20, 1989 under accession number NCIMB 40239.

d) Plasmid pCYC-TAT (FIG. 6)

The XbaI - SalI fragment from the synthetic tat gene in mpII TAT was cloned between the Xba I and SalI sites of an M13 derivative carrying the polylinker sequence shown below:

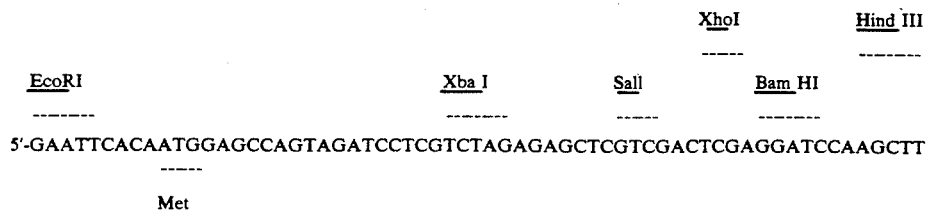

In the resulting clone, mpACIE-TAT, the sequence between the ATG codon underlined and the Xba I site was chosen for optimal codon usage in yeast and to remove the NcoI site in the original mpll-TAT clone. The EcoRI - Bam HI fragment carrying the entire tat coding sequence was then transferred from mpACIE-TAT into the plasmid pEX-2d Eco. (FIG. 5, NCIMB 40242), between the Eco RI and Bam HI site to produce pCYC-TAT (FIG. 6).

In this plasmid, transcription of the tat gene is under the control of the cvcl promoter, transcription terminates at the cvcl terminator downstream of the tat gene.

Transformed E.Coli DHI cells containing plasmid pEX-2d Eco were deposited under the terms of the Budapest Treaty at the National Collection of Industrial and Marine Bacteria on 20th December 1989 under accession number NCIMB 40242.

e) Plasmid pATZCT (FIG. 7)

The NcoI - BglII fragment carrying the prombter, tat gene and terminator from pCYC - TAT was excised by digestion with NcoI and BglII. The 3-recessed ends of the fragment were extended by using DNA polymerase Klenow fragment and a mixture of dATP, dCTP, dGTP and dTTP to produce a flush-ended, double stranded fragment. This was then ligated into the plasmid plO14/2 (FIG. 4) using the NruI site to produce pATZCT (FIG. 7).

f) Plasmid pER 984 (FIG. 8)

In the plasmid pER984, a synthetic tat gene is transcribed from the qal10 promoter, which is induced by growth on galactose (M. Johnston et al, Mol. Cell.

the α-factor mRNA, such that authentic TAT, without the α-factor pre-pro-sequence is produced.

To construct pMWα-TAT, oligonucleotide adaptors are used to allow the cloning of the tat gene into the α-factor promoter plasmid as a Hind III fragment.

The ADHI transcription terminator was inserted between HindIII and BamHI sites in a derivative of pJDB207 in which the HindIII site in the 2μ region had been deleted. An EcoRI-HindIII fragment carrying the entire α-factor promoter and prepro leader sequence was inserted immediately upstream from the terminator. A second HindIII site was introduced within the alpha-factor promoter by primer-directed mutagenesis (an A to C mutation at position -43 relative to the A of the initiator codon, as described by Carter et al in "DNA Cloning". Vol.3. 141-161[D M Glover Ed.]. The BamHI site at the 3,-end of the ADH terminator and the SalI site in the remnant of TetR the T gene (see Methods in Enzymology, 101, 320–321) were each deleted (in separate experiments) by digestion, treatment with Klenow fragment and religation. A HindIII fragment containing a SalI site was inserted between the HindIII sites such that the SalI site was adjacent to the downstream HindIII site (i.e. that at the 5'-end of the terminator). This downstream HindIII site was then deleted by partial digestion, Klenow treatment and religation. The tat gene was then inserted as HindIII-SalI fragment, prepared as described below, to provide pMWα-TAT.

mpll-TAT was modified by insertion of a synthetic linker at the 5'-end of the tat gene, using the NcoI site as shown, to produce mpAFIE-TAT.

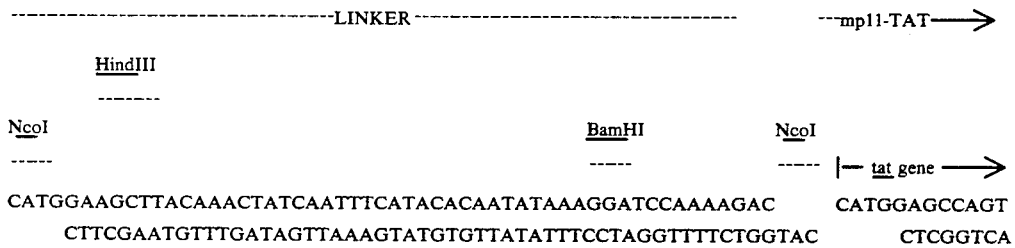

Biol., 1984, 4, 1440). The tat gene is assembled using overlapping synthetic fragments synthesized using beta-cyanoethyl-phosphoramidites (Biosearch, N. D. Sinha et al, Nucl. Acids Res., 1984, 12, 4539).

The sequence of the synthetic tat gene differed from authentic tat of the HIV-I λ BH10 variant (L. Ratner, Nature, 1985, 313, 277) in codons for Arg 7 (AGA to CGT, to create an Xba I site), Tyr 47 (TAT to TAC-)and Arg 55 (CGA to CGT, to introduce a Sal I site). Furthermore, a NcoI site was placed at a position corresponding to the translational start codon (CCATGG). The presence of SstI and PstI overhangs at the 5'- and 3'- ends of the synthetic tat segment allowed its convenient cloning into M13mpll. To construct pER984, tat was excised from mpll-TAT for double -stranded phage DNA on an EcoRI - Hind III fragment and ligated to the BamHI-Eco RI fragment of pBM150, which carries the galIO promoter and the large BamHI-Hind III fragment of JDB207 (J D Beggs, Molecular Genetics in Yeast, ed. von Wettstein et al).

g) Plasmid p MWα-TAT (FIG. 9)

The plasmid pMWα-TAT was constructed to allow constitutive tat expression from the α-factor promoter (J Kurjan et al, Cell, 1983, 30,933). In pMWα-TAT, the tat gene was inserted into the 5'-untranslated region of Transfer of the tat gene from mpAFIE-TAT as this HindIII-SalI fragment, reconstituted the α-factor promoter sequence in pMWeTAT (up to the ATG of the prepro sequence), but not the remainder of the prepro leader sequences, which had been deleted on insertion of the HindIII linker containing the SalI site. This allowed intracellular expression of authentic TAT protein without the α-factor leader sequence.

3) Growth of yeast cells

Yeast strains, such as Saccharomyces Cerevisiae BJ1991 (genotype:α, pep 4-3, prbl-1122, ura 3-52, leu 2, trp 1 (GAL+)), were transformed with plasmid DNA, and cultured, by standard methods essentially as described by sherman et al in "Methods in Yeast Genetics" (Cold Spring Harbor laboratory, New York, 1981). The yeast expression plasmids described above carried either the TRPI or URA3 markers which can complement the trp and ura auxotrophic markers in BJ1991. Therefore, transformants in BJ1991 were selected by their ability to grow on media lacking either tryptophan or uracil, or both compounds, depending on the plasmid used.

BJ1991 cells carrying the plasmids pATZCT (FIG. 7) or plO14/2 (FIG. 4) were grown in glucose minimal medium (prepared as described in Sherman et al) supplemented with leucine and uracil (50μg/ml each) but lacking in tryptophan, at 30° C. with gentle agitation. BJ1991 cells containing pCYC-TAT only, were grown in glucose minimal medium supplemented with leucine and tryptophan (each at 50μg/ml) but lacking uracil. BJ1991, cells carrying both pCYC-TAT and p1014/2 were grown in glucose minimal medium supplemented with leucine at 50μg/ml but lacking tryptophan and uracil. BJ1991 cells carrying both pER984 and p1014/2 were grown either in glucose minimal medium or galactose minimal media, both supplemented with leucine at 50mg/ml but lacking tryptophan and uracil. Glucose minimal medium contains glucose (2% (w/v), yeast nitrogen base, (0.067 g/100 ml), but does not contain amino acids. Galactose minimal media contains galactose (2% w/v), glucose (0.01% amino acids solid glucose minimal medium additionally contains agar (2%(w/v)).

S.cerevisae BJ1991 was deposited under the terms of the Budapest Treaty at the National Collection of Industrial and Marine Bacteria on Dec. 20, 1989 under the accession number NCIMB 40243.

4) Measurement of β-galactosidase activity in cell-free extracts i) Growth of cells S. cerevisiae BJ1991 transformants containing either pATZCT, pCYC-TAT, p1014/2, both pCYC-TAT and p1014/2 or both pER984 and p1014/2 were grown overnight, from a 1:100 inoculum, at 30C to an A550 of 0.5-1.5 (late logarithmic phase) in the appropriate medium as described above.

ii) Preparation of cell-free extracts

Cells were kept over ice to minimise protein degradation. Cells were pelleted from 1 volume of culture by low-speed centrifugation (5000g for 15 min.) and then resuspended in 1 volume of phosphate buffered saline (PBS). Cells were re-pelleted as before and resuspended in 0.05 vol of PBS. The cell suspension was vortexed twice for 30 sec, after the addition of an equal volume of glass beads (0.4 mm, 40 mesh), with cooling on ice between treatments. The mixture was decanted into Eppendorf tubes, centrifuged for 1 min and then the supernatant was removed for assay.

The protein concentration in supernatant samples was determined using the Bio-Rad protein assay kit according to the manufacturer's instructions.

iii) β-Galactosidase Assays

β-Galactosidase assays were performed as follows: Samples of the cell-free extracts (1 to 50 μl) were removed and the volumes were adjusted to 50 μl with PBS. Each 50μl sample was added to 300 ul of reaction mix, prewarmed to 37° C., which contained 60mM Na2HP04.7H20, 40mM NaH2P04.7H20, 1 mM KCl, 1 mM MgS04.7H20, 50 mM betamercaptoethan and 0.9 mg/ml ortho nitro phenyl β-D galactopyranoside (ONPG) (pH7.0). Samples were incubated at 37C for timed intervals until a yellow colouration appeared. Then 500 μl of 1M Na2CO3 was added to terminate the reaction and the absorbance of the solution at 420 nanometers (A420) was measured. The rate of increase in A420 was compared to that obtained using commercial beta-galactosidase and figures for the yeast extracts were calculated as beta-galactosidase units/mg protein.

Samples were usually assayed in quadruplicate. Typical results are shown below:

| Strain of S. cerevisiae | Plasmid | β-Galactosidase activity units × $10^{-2}$/mg protein |
|---|---|---|
| BJ1991 | p1014/2 | 0.9+/−0.0 |
| BJ1991 | p1014/2 + pCYC-TAT | 14.9+/−4.6 |
| BJ1991 | pCYC-TAT | 0.9+/−0.0 |
| BJ1991 | pAZTCT | 5. +/−0.6 |
| BJ1991 | p1014/2 + pER 984 | 3.9+/−0.9 (glucose minimal media) |
| BJ1991 | p1014/2 + pER 984 | 15.7+/−0.9 (Galactose minimal media) |

The difference in activity observed between cells carrying pAZTCT and cells carrying p1014/2 +pCYC-TAT is probably due to the higher copy number of the pCYC-TAT plasmid (which carries the 2μ origin of replication) compared to pAZTCT (a centromeric vector) which should result in higher levels of TAT production in the former strain and therefore in higher levels of beta-galactosidase. However pAZTCT is the preferred plasmid because, being centromeric, it exhibits greater stability than the pl014/2 +pCYC-TAT co-transformant (in terms of production of beta-galactosidase activity) when cultured continuously.

5) Detection of β-Galactosidase activity using whole-cells

The TAT-induced β-Galactosidase activity can also be demonstrated in a more convenient manner by growing cells in media which contain a chromogenic substrate such as X-Gal or CPRG. The example below describes the use of X-Gal. Overnight cultures grown to an A550 of 1.0–2.0 in the appropriate medium as described above were diluted 1:100 into "X-Gal" medium, which contained 0.1 M KH2P04, 0.015M (NH4)2 S04, 0.075M KOH, 0.8 mM MgS04, 0.002 mM Fe2(SO4)3, glucose (2%, wt/vol) 0.4 μg/ml thiamine, 0.4 μg/ml pyridoxine, 0.4 μg/ml pantothenic acid, 2ag/ml inositol, 0.02 μg/ml biotin, 2% agar and 400μg/ml X-Gal (5-bromo-4-chloro-3-indolyl-beta-D-galactopyranoside) supplemented with leucine or uracil as described above, held at 40° C. 350 ml Aliquots were dispensed into the wells of a 96-well microtitre plate and the plate was incubated at 30° C. for 3–5 days. Typical results can be described qualitatively as follows:

| Strain of S. cerevisiae | Plasmid | Colour of well after 5 days |
|---|---|---|
| BJ1991 | p1014/2 | turbid/colourless (white) |
| BJ1991 | p1014/2 + pCYC-TAT | turbid/blue |
| BJ1991 | pCYC-TAT | turbid/colourless (white) |
| BJ1991 | pAZTCT | turbid/blue |

In this system, samples may be tested for their ability to inhibit tat activity by being deposited, in suitable form, in the wells of the microtitre plate before addition of the yeast/molten agar mixture. Compounds which inhibit tat activity should reduce the development of the blue colouration, without greatly affecting the growth of the cells. Non-tat-specific compounds which are toxic to yeast or which inhibit β-galactosidase activity or the activity of the act or cvc promoters can be detected using suitable secondary assays.

TABLE 1

| Seq. ID No.: | 1 |
|---|---|
| Sequence Type: | Nucleotide with corresponding protein |

TABLE 1-continued

| | |
|---|---|
| Sequence Length: | 261 base pairs |
| Strandedness: | Double |
| Topology: | Linear within a circular plasmid |
| Molecule Type: | Synthetic DNA |

7

5'- ATG GAG CCA GTA GAT CCT CGT CTA GAG CCC TGG AAG CAT CCA GGA AGT
Met Glu Pro Val Asp Pro Arg Leu Glu Pro Trp Lys His Pro Gly Ser
CAG CCT AAA ACT GCT TGT ACC AAT TGC TAT TGT AAA AAG TGT TGC TTT
Gln Pro Lys Thr Ala Cys Thr Asn Cys Tyr Cys Lys Lys Cys Cys Phe
                                                                47
CAT TGC CAA GTT TGT TTC ATA ACA AAA GCC TTA GGC ATC TCC TAC GGC
His Cys Gln Val Cys Phe Ile Thr Lys Ala Leu Gly Ile Ser Tyr Gly
        55
AGG AAG AAG CGG AGA CAG CGT CGA AGA CCT CCT CAA GGC AGT CAG ACT
Arg Lys Lys Arg Arg Gln Arg Arg Arg Pro Pro Gln Gly Ser Gln Thr
CAT CAA GTT TCT CTA TCA AAG CAA CCC ACC TCC CAA TCC CGA GGG GAC
His Gln Val Ser Leu Ser Lys Gln Pro Thr Ser Gln Ser Arg Gly Asp
CCG ACA GGC CCG AAG GAA TAG - 3'
Pro Thr Gly Pro Lys Glu

TABLE 2

(Portion 1)

| | |
|---|---|
| Seq. ID No.: | 2 |
| Sequence Type: | Nucleotide |
| Sequence Length: | 50 base pairs having two single strand overhangs of, respectively, 4 and 9 bases |
| Strandedness: | Double and single |
| Topology: | Linear |
| Molecule Type: | Synthetic DNA |

TAT/1A

```
        SstI NcoI                                                XbaI
          CCATGG  AGCCAGTAGA  TCCTCGTCTA    GAGCCCTGGA  AGCATCCAGG   AAGTCAGCCT  AAA-3'
5'-TCGAGGTACC  TCGGTCATCT  AGGAGCAGAT    CTCGGGACCT  TCGTAGGTCC   TTCA
                                      TAT/1B
```

| | |
|---|---|
| Seq. ID No.: | 3 |
| Sequence Type: | Nucleotide |
| Sequence Length: | 49 base pairs having two single strand overhangs of 9 bases |
| Strandedness: | Double and single |
| Topology: | Linear |
| Molecule Type: | Synthetic DNA |

TAT/2A

```
           A  CTGCTTGTAC  CAATTGCTAT  TGTAAAAAGT  GTTGCTTTCA  TTGCCAAGTT  TGTTTCA-3'
5'- GTCGGATTTT  GACGAACATG  GTTAACGATA  ACATTTTTCA  CAACGAAAGT  AACGGTTC
                                      TAT/2B
```

| | |
|---|---|
| Seq. ID No.: | 4 |
| Sequence Type: | Nucleotide |
| Sequence Length: | 49 base pairs having two single strand overhangs of, respectively, 4 and 9 bases |
| Strandedness: | Double and single |
| Topology: | Linear |
| Molecule Type: | Synthetic DNA |

TAT/3A

```
                                                                            SalI
           T  AACAAAAGCC  TTAGGCATCT  CCTACGGCAG  GAAGAAGCGG  AGACAGCG
5'- AAACAAAGTA  TTGTTTTCGG  AATCCGTAGA  GGATGCCGTC  CTTCTTCGCC  TCTGTCGCAG    CT-3'
                                      TAT/3B
```

(Portion 2)

| | |
|---|---|
| Seq. ID No.: | 5 |
| Sequence Type: | Nucleotide |
| Sequence Length: | 49 base pairs having two single strand overhangs of, respectively, 4 and 9 bases |
| Strandedness: | Double and single |
| Topology: | Linear |
| Molecule Type: | Synthetic DNA |

```
     Sal I                                        TAT/4A
5'-TCGAAGACCT    CCTCAAGGCA  GTCAGACTCA  TCAAGTTTCT  CTATCAAAGC    AA -3'
     TCTGGA      GGAGTTCCGT  CAGTCTGAGT  AGTTCAAAGA  GAT
                                      TAT/4B
```

| | |
|---|---|
| Seq. ID No.: | 6 |
| Sequence Type: | Nucleotide |
| Sequence Length: | 62 base pairs having two single strand overhangs of, respectively, 4 and 9 bases |
| Strandedness: | Double and single |
| Topology: | Linear |
| Molecule Type: | Synthetic DNA |

TAT/5A

```
           C  CCACCTCCCA  ATCCCGAGGG  GACCCGACAG  GCCCGAAGGA  ATAGTAACTA
5' - AGTTTCGTTG  GCTGGAGGGT  TAGGGCTCCC  CTGGGCTGTC  CGGGCTTCCT  TATCATTGAT
```

TABLE 2-continued

|  | SalI | PstI |
|---|---|---|
|  | ACTAAGTCGA | CTGCA -3' |
|  | TGATTCAGCT | G |

TAT/5B

TABLE 3

(Portion 1)

| Seq. ID No.: | 7 |
|---|---|
| Sequence Type: | Nucleotide |
| Sequence Length: | 54 base pairs having two single strand overhangs of, respectively, 4 and 9 bases |
| Strandedness: | Double and single |
| Topology: | Linear |
| Molecule Type: | Synthetic DNA |

```
       EcoRI amHI                                      PvuII
5'-AATTCGGATC CTGCATATAA CAGCTGCTT  TTTGCCTGTA CTGGGTCTCT CTGGTTAG
        GCCTAG GACGTATATT CGTCGACGAA AAACGGACAT GACCCAGAGA GACCAATCTG GTCTAGA -3'
                                        TAR/1B
```

(Portion 2)

| Seq. ID No.: | 8 |
|---|---|
| Sequence Type: | Nucleotide |
| Sequence Length: | 53 base pairs having two single strand overhangs of, respectively, 4 and 9 bases |
| Strandedness: | Double and single |
| Topology: | Linear |
| Molecule Type: | Synthetic DNA |

```
         GglII            SstI
5' - ACCAGATCTG    AGCCTGGGAG CTCTCTGGCT AACTAGGGAA CCCACTGCTT AAGCCTCAAT    AA
              C    TCGGACCCTC GAGAGACCGA TTGATCCCTT GGGTGACGAA TTCGGAGTTA    TTTCGA -3'
                                                                              HindIII
                                           TAR/2B
```

---

We claim:

1. A transformed S.cerevisiae yeast cell containing the following DNA sequences,
   an HIV tat gene coding for a TAT protein,
   a first promoter exercising transcriptional control over the tat gene,
   an HIV regulatory control sequence which is responsive to the TAT protein,
   a pre-selected gene coding for a desired polypeptide or protein, the pre-selected gene being under the control of the HIV regulatory control sequence, and
   a second promoter exercising transcriptional control over the HIV regulatory control sequence and the pre-selected gene.

2. A yeast cell according to claim 1 wherein the first promoter is a yeast promoter.

3. A yeast cell according to claim 2 wherein the first promoter is selected from the yeast promoters gal 10, cycI and α-factor.

4. A yeast cell according to claim 1 wherein the second promoter is a yeast promoter.

5. A yeast cell according to claim 4 wherein the second promoter is the yeast promoter S.cerevisiae act-1.

6. A yeast cell according to claim 1 wherein the HIV regulatory control sequence is a TAT responsive TAR sequence.

7. A yeast cell according to claim 1 wherein the pre-selected gene codes for an indicator protein.

8. A yeast cell according to claim 7 wherein the indicator protein is selected from β-galactosidose, chloramphenicol acetyltransferase and IL2.

9. A yeast cell according to claim 8 wherein the indicator protein is β-galactosidase.

10. A gene expression system comprising
    an HIV tat gene coding for a TAT protein,
    a first yeast promoter exercising transcriptional control over the tat gene,
    an HIV regulatory control sequence which is responsive to the TAT protein,
    a pre-selected gene coding for a desired polypeptide or protein, the pre-selected gene being under the control of the HIV regulatory control sequence,
    and a second yeast promoter exercising transcriptional control over the HIV regulatory control sequence and the pre-selected gene.

11. A gene expression system according to claim 10 wherein the system is one transfer vector.

12. A gene expression system according to claim 10 wherein the system is two transfer vectors, the first vector containing the HIV tat gene and the first yeast promoter and the second vector containing the HIV regulatory control sequence, the pre-selected gene and the second yeast promoter.

13. A method of producing a desired polypeptide protein comprising cultivating a transformed S.cerevisiae yeast cell containing the following DNA sequences,
    an HIV tat gene coding for a TAT protein,
    a first promoter exercising transcriptional control over the tat gene,
    an HIV regulatory control sequence which is responsive to the TAT protein,
    a pre-selected gene coding for a desired polypeptide or protein, the pre-selected gene being under the control of the HIV regulatory control sequence,
    and a second promoter exercising transcriptional control over the HIV regulatory control sequence and the pre-selected gene.

14. A method of obtaining TAT protein mediated expression of a pre-selected gene under the control of an HIV regulatory control sequence which comprises cultivating a transformed S.Cevevisige yeast cell containing the following DNA sequences
    an HIV tat gene coding for a TAT protein,
    a first promoter exercising transcriptional control over the tat gene,
    an HIV regulatory control sequence which is responsive to the TAT protein,
    a pre-selected gene coding for a desired polypeptide or protein, the pre-selected gene being under the control of the HIV regulatory control sequence,
    and a second promoter exercising transcriptional control over the HIV regulatory control sequence and the pre-selected gene.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 261 nucleotides
        ( B ) TYPE: nucleic acid
        ( C ) STRANDEDNESS: double
        ( D ) TOPOLOGY: linear within a circular plasmid ( i i ) MOLECULE TYPE: Synthetic DNA ( i i i ) HYPOTHETICAL: No.

( i v ) ANTI-SENSE: No.

( v ) FRAGMENT TYPE: internal fragment ( i x ) FEATURE: Sequence differs from authentic tat of
        the HIV-1 1 BH10 variant at codons for
        Arg 7 (AGA to CGT, to
        create an XbaI site), Tyr 47 (TAT to
        ( T A C ) and Arg 55 (CGA to CGT).

( x i ) SEQUENCE DESCRIPTION: SEQ ID NO: 1:

```
ATG  GAG  CCA  GTA  GAT  CCT  CGT  CTA  GAG  CCC  TGG  AAG  CAT  CCA  GGA  AGT    48
Met  Glu  Pro  Val  Asp  Pro  Arg  Leu  Glu  Pro  Trp  Lys  His  Pro  Gly  Ser
               5                        10                       15

CAG  CCT  AAA  ACT  GCT  TGT  ACC  AAT  TGC  TAT  TGT  AAA  AAG  TGT  TGC  TTT    96
Gln  Pro  Lys  Thr  Ala  Cys  Thr  Asn  Cys  Tyr  Cys  Lys  Lys  Cys  Cys  Phe
              20                        25                       30

CAT  TGC  CAA  GTT  TGT  TTC  ATA  ACA  AAA  GCC  TTA  GGC  ATC  TCC  TAC  GGC   144
His  Cys  Gln  Val  Cys  Phe  Ile  Thr  Lys  Ala  Leu  Gly  Ile  Ser  Tyr  Gly
              35                        40                       45
```

-continued

| AGG | AAG | AAG | CGG | AGA | CAG | CGT | CGA | AGA | CCT | CCT | CAA | GGC | AGT | CAG | ACT | 192 |
| Arg | Lys | Lys | Arg | Arg | Gln | Arg | Arg | Arg | Pro | Pro | Gln | Gly | Ser | Gln | Thr | |
| | 50 | | | | 55 | | | | | | 60 | | | | | |
| CAT | CAA | GTT | TCT | CTA | TCA | AAG | CAA | CCC | ACC | TCC | CAA | TCC | CGA | GGG | GAC | 240 |
| His | Gln | Val | Ser | Leu | Ser | Lys | Gln | Pro | Thr | Ser | Gln | Ser | Arg | Gly | Asp | |
| 65 | | | | | 70 | | | | | 75 | | | | | 80 | |
| CCG | ACA | GGC | CCG | AAG | GAA | TAG | | | | | | | | | | 261 |
| Pro | Thr | Gly | Pro | Lys | Glu | | | | | | | | | | | |
| | | | | 85 | | | | | | | | | | | | |